United States Patent [19]

Kenyon et al.

[11] Patent Number: 4,784,130
[45] Date of Patent: Nov. 15, 1988

[54] FLOW CONTROLLER

[75] Inventors: Franklin D. Kenyon, Williamsville; John W. Puckhaber, Lakeview, both of N.Y.

[73] Assignee: The John Bunn Company, Tonawanda, N.Y.

[21] Appl. No.: 937,730

[22] Filed: Dec. 4, 1986

[51] Int. Cl.⁴ ............................................. A61M 16/00
[52] U.S. Cl. ..................... 128/204.21; 128/204.23; 128/204.26
[58] Field of Search ................ 128/204.18, 204.21, 128/204.23, 204.26, 203.12

[56] References Cited

U.S. PATENT DOCUMENTS

| | | | |
|---|---|---|---|
| 3,383,484 | 5/1968 | Arp et al. | 128/204.23 |
| 3,467,137 | 9/1969 | Brown | 169/473 |
| 3,489,144 | 1/1970 | Dibelius et al. | 128/205.12 |
| 3,503,393 | 3/1970 | Manley | 128/204.26 |
| 3,526,239 | 9/1970 | Oroza | 128/205.12 |
| 3,552,392 | 1/1971 | Dounoucos et al. | 128/204.26 |
| 3,584,621 | 6/1971 | Bird et al. | 128/204.26 |
| 3,611,178 | 10/1971 | McConnell | 128/204.23 |
| 3,913,576 | 10/1975 | Martin et al. | 128/205.12 |
| 3,952,739 | 4/1976 | Cibulka | 128/204.23 |
| 4,003,377 | 1/1977 | Dahl | 128/204.23 |
| 4,050,458 | 9/1977 | Friend | 128/204.23 |
| 4,127,123 | 11/1978 | Bird | 128/145.8 |
| 4,127,129 | 11/1978 | Cramer | 128/205.12 |
| 4,176,663 | 12/1979 | Hewlett | 128/204.26 |
| 4,206,754 | 6/1980 | Cox et al. | 128/204.26 |
| 4,215,681 | 8/1980 | Zalkin et al. | 128/204.21 |
| 4,232,665 | 11/1980 | Vaseen | 128/200.24 |
| 4,239,039 | 12/1980 | Thompson | 128/204.18 |
| 4,269,216 | 5/1981 | Sullivan et al. | 128/200.24 |
| 4,334,532 | 6/1982 | Jackson | 128/204.26 |
| 4,340,045 | 7/1982 | Manley | 128/204.26 |
| 4,401,115 | 8/1983 | Monnier | 128/204.26 |
| 4,414,982 | 11/1983 | Durkhan | 128/204.26 |
| 4,428,372 | 1/1984 | Beysel et al. | 128/204.22 |
| 4,519,387 | 5/1985 | Durkhan et al. | 128/204.26 |
| 4,584,996 | 4/1986 | Blum | 128/204.21 |
| 4,648,395 | 3/1987 | Sato et al. | 128/204.23 |
| 4,665,911 | 5/1987 | Williams et al. | 128/204.23 |
| 4,686,975 | 8/1987 | Naimon et al. | 128/204.23 |

FOREIGN PATENT DOCUMENTS

| | | |
|---|---|---|
| 0188071 | 7/1986 | European Pat. Off. . |
| 452120 | 5/1968 | Switzerland . |
| 1146683 | 3/1969 | United Kingdom . |
| 2162756 | 2/1986 | United Kingdom . |
| 2164568 | 3/1986 | United Kingdom . |

OTHER PUBLICATIONS

Vario Sonic AG–Automatic Flow Control Device (O2–Cannula Controller)–Advertisement Photo's of a Demand Valve by Djon Biermar, which corresponds to the Vario Sonic AG advertisement.

Primary Examiner—Edward M. Coven
Assistant Examiner—J. P. Lacyk
Attorney, Agent, or Firm—Roylance, Abrams, Berdo & Goodman

[57] ABSTRACT

An oxygen flow controller for use in administering oxygen from a pressure-regulated source on demand to a patient through a nasal cannula is disclosed. A flow path is opened by a solenoid valve in response to the negative pressure created in the nasal canula by the patient's inhalation. The valve is opened for the interval needed to maintain an inhalation to exhalation ration of one-to-two, and the timing cycle and the open and closed duration times of the valve are made to automatically match the patient's breathing.

9 Claims, 4 Drawing Sheets

FLOW CONTROLLER

FIELD OF THE INVENTION

This invention relates to the control of flows of pressurized gas. More particularly, the invention relates to the administration of oxygen for medical reasons from a pressure-regulated source to a patient, and in particular to such administration of oxygen using a nasal cannula.

BACKGROUND OF THE INVENTION

Generally, oxygen is delivered from a pressure-regulated source at a continuous flow rate prescribed by a physician. These pressure-regulated sources include large stationary oxygen cylinders, small portable oxygen cylinders, stationary liquid oxygen reservoirs, small portable liquid oxygen containers, oxygen concentrators, and oxygen piped through hospital walls.

Since the respiration cycle is approximately one-third inhalation and two-thirds exhalation, and oxygen provided during exhalation does not benefit the patient, a substantial amount of oxygen is wasted during exhalation.

Previously, flow control valve devices administered oxygen via a respirator, or scuba type equipment required a face mask in order to detect inspiration. Devices with adequate sensitivity to detect inhalation through a nasal cannula could not distinguish negative pressures produced by inhalation from those that occurred as a result of the valve opening and closing. Some devices avoided this problem by delivering a fixed volume of oxygen very early in the inspiration cycle, but the amount of oxygen required varies from patient to patient. It is generally accepted that the best treatment is the one that is the most like normal breathing and at the same time maintains as close to normal oxygen saturation in the patient's blood as possible.

OBJECTIVES AND ADVANTAGES OF THE INVENTION

The present invention senses the start of the patient's inhalation with a negative pressure-sensing device connected to the patient's nasal cannula and opens a solenoid valve that allows a pressure-regulated source of oxygen to flow oxygen through the cannula to the patient. The period of time the valve is kept open is determined by the patient's breathing. The inhalation to exhalation (I/E) ratio is assumed to average one half. Upon sensing the patient's first breath, the valve is opened for a period equal to one half of the time between power up and the first breath. Thereafter, oxygen will be supplied for a period of time equal to half the duration of the previous exhalation.

At the estimated end of the inspiration cycle, the valve is closed and a timer is started. When the patient's next breath is sensed, the valve is opened for the interval required to maintain the 50% I/E ratio.

A principal object of the present invention is to provide a device that will reduce the amount of oxygen that is normally wasted when supplemental oxygen is prescribed to restore the oxygen saturation of a respiratory patient's blood.

Another object of this invention is to provide an apparatus that will extend the period of time that a respiratory patient can ambulate with a portable oxygen supply.

SUMMARY OF THE INVENTION

The invention provides methods and apparatus for achieving the above objectives and advantages. In particular, the invention comprises a pressure sensor which works with a diaphragm and proximity switch. In addition, the invention flow controller includes control circuitry having features which cooperate with the pressure sensor in order to achieve the advantages and objectives of the invention.

More specifically, the pressure sensor according to the invention is arranged so that the negative pressure from the patient operates on the diaphragm on the side thereof opposite the proximity switch. The diaphragm carries a metal disk which faces the proximity switch and activates it upon the motion of the diaphragm to and fro with respect to the proximity switch in response to the pressure pulses on the side of the diaphragm opposite the switch.

The housing of the pressure sensor on the side of the diaphragm which carries the switch is beveled or dished, which greatly prolongs the useful life of the diaphragm and which permits the pressure sensor of the invention to operate with much larger pressures than it could tolerate were sharp edges provided at this juncture. Another advantage which results from the structure is that, by having the proximity switch and the negative pressure on opposite sides of the diaphragm, the surface of the diaghragm exposed to the negative pressure is thereby maximized which increases the sensitivity and general performance characteristics of the invention pressure sensor.

In addition, the diaphragm is mounted within the sensor housing relatively loosely. This assures that the metal disk will be either cleanly in or cleanly out of electrical cooperation with the proximity switch. A portion of the control circuitry, described below, assures that this looseness in the diaphragm will not result in any undesirable performance characteristics as could occur were not that looseness accommodated by the circuitry.

Some prior art flow controllers (which are also known, inaccurately, as "demand valves") operate on analog logic. The present invention is based on a digital system in its control circuitry. This, as is well known to those skilled in the electronics arts, produces significant advantages for the present invention in the fields of cost, accuracy, reliability, power consumption, and the like.

The control circuitry of the invention includes numerous features and methods of operation which cooperate with the improved pressure sensor in achieving the advantages of the invention over the prior art and in meeting its objectives. More specifically, the circuitry includes two "clocks", one called the fast clock and the other called the slow clock. For the indicated desirable ratio of 2:1 of exhalations to inhalations, the two clocks are made to operate in a ratio of 2:1. If another ratio is desired for a particular patient or in some other environment, the rates or frequencies of both clocks are manually adjustable, and thus any ratio can be achieved.

The circuitry includes an arrangement of a steering circuit and a latch which operate by causing the pulses from the slow clock to correspond to the time of exhalation, and the pulses from the fast clock to correspond to the time of inhalation. An up/down counter is provided, and this up/down counter provides a pulse which ultimately controls the supply valve between the pressure-regulated oxygen source and the patient.

This array of clocks and steering circuit assures that whatever time oxygen is supplied to the patient will be equal to half of the time of the previous exhalation of the patient. This automatically accommodates to the duration of the patient's cycle. That is, one patient when breathing normally may inhale every six seconds, and another every eight seconds, and the invention will automatically accommodate.

In addition, upon start-up, this same counting circuit will automatically "home" to match the frequency of the patient's breathing. This occurs due to the "rule" of the invention circuitry of causing each inhalation to be equal to one half of the time of the previous exhalation. The correction has the appearance of a damped sinusoidal curve, and will match the patient's breathing, both as to duration and frequency, within 30 to 60 seconds.

This same circuitry will automatically accommodate irregularities, such as a sudden gasp, or any other aberration in the patient's breathing. The system of the invention flow controller and the patient both inherently create certain spurious pulses which occur at the beginning of each expiration breath of the patient. The invention circuitry accommodates this by providing a blanking signal which disables the oxygen control valve for the period of time such spurious pulses normally appear, to thus insure the accuracy of the operation of the invention device overall.

Another feature of the invention has to do with an alarm circuit. This alarm circuit is usually used only in stationary equipment, rather than in portable equipment. It can, however, be used in portable equipment, but this is not thought to be necessary since the patient is usually awake, and the addition of the alarm will extract a "price" in terms of added weight and electrical power consumption.

During normal operation the timer will provide an alarm if more than a preset time—30 seconds has been set more or less arbitrarily—elapses between two inhalation breaths of the patient. Another feature of the alarm is that it will automatically reset. That is, for example, if the patient wishes to remove the cannula for personal or other reasons for a short period of time, he does so, pushes the alarm reset button, and goes about his business. Upon return to use of the cannula, his next inhalation will activate the proximity switch in the sensor, which in turn is caused through the circuitry to automatically enable the alarm again. The countdown time of this alarm timer can be manually set to match the needs of a particular patient or a particular environment.

The invention thus provides a flow controller which eliminates the prior art waste of oxygen in this medical environment. The advantages flowing from this elimination of waste are enormous. An oxygen concentrator can be made smaller and lighter weight. The same size bottle or tank of oxygen will last three times as long as would the same apparatus without the invention flow controller. Portable units can permit patients to be ambulatory three times as long as they would be by the same apparatus without the invention flow controller.

Another advantage of the sensor's physical arrangement of having the proximity switch on the opposite side of the diaphragm from the gas flow is that the surging which occurs upon activation of the control valve tends not to cause fluttering and thus will cause the necessary rapid activation and deactivation of the metal disk with respect to the proximity switch.

Another feature of the invention design in the sensor itself is that the weight and size of the metal disk have been made as small as possible. This is an advantage, since the total weight and mass to be moved by each inspiration breath of the patient is thereby minimized. Since the persons with whom the invention flow controller is used are almost always ill, these inspiration breaths can be very weak, and the light weight of the part of the sensor which moves in response to their breathing is an advantage and improves the sensitivity and operating characteristics of the invention sensor.

While the invention has been designed particularly for use with a nasal cannula, it can also be used with face masks and any other apparatus. That is, the invention is sensitive enough to work even with the very slight pressures generated in a nasal cannula, and thus is operable with face masks and other apparatuses and in other environments, where the negative pressure created by the patient's breathing is stronger.

Another feature of the invention has to do with an interaction between the loosely mounted diaphragm and the electronics. The sensitivity of the invention sensor is greatly increased, but a potential problem is that the lack of tension on the diaphragm could permit the sensor diaphragm to retrigger by itself. In order to narrow the "window" during which the sensor could trigger the valve to open, the electronics permit the triggering pulse from the proximity switch to open the flow control valve upon the presence of a negative pressure, but only if such a negative pressure follows a positive pressure. The positive pressure could be caused by the patient's exhalation or by the rush of oxygen caused by the previous inhalation. Thus, the electronics and the loose diaphragm together ensure proper cyclical operation of the flow control valve.

Looking at it another way, the positive pressure of the exhalation or the rush of oxygen in effect arms the circuitry, and the next following negative pressure (inhalation) causes it to operate and supply oxygen for that same inhalation breath.

Thus there is provided a composite physical pressure sensor and an electronic circuit which together constitute a flow controller particularly adapted to operate with a pressure-regulated oxygen supply to achieve numerous advantages over the prior art, which is highly reliable in use, which largely eliminates the heretofore common waste of oxygen, and which achieves enormous advantages over the prior art flowing from this elimination of waste, while at the same time providing a highly reliable and rugged device eminently suitable for its field of application.

BRIEF DESCRIPTION OF THE FIGURES OF THE DRAWING

The invention will be understood more clearly with reference to the accompanying drawing, which drawing also forms a part of this disclosure, wherein.

DETAILED DESCRIPTION OF THE PREFERRED EMBODIMENT

Figure 1:
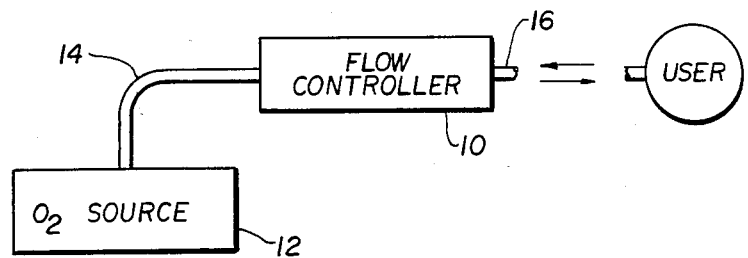
FIG. 1 is a highly simplified schematic drawing showing the field of application of the invention flow controller.

In the description herein, like parts are indicated throughout the specification and drawings with the same reference numerals. The figures are not drawn to scale. In some cases portions have been exaggerated in order to more clearly depict the features of the invention.

Referring now in detail to FIG. 1, the invention flow controller 10 receives oxygen from a source 12 which may be any pressure-regulated source of oxygen. For example, the source 12 can be a large or a small bottle or tank of pressurized oxygen, an oxygen concentrator, an oxygen tap as is commonly available in hospitals in the walls near the patients' beds, or any other such source. The source 12 is connected to the flow controller 10 by a line 14, and a line 16 delivers the oxygen to the user.

Figure 2:
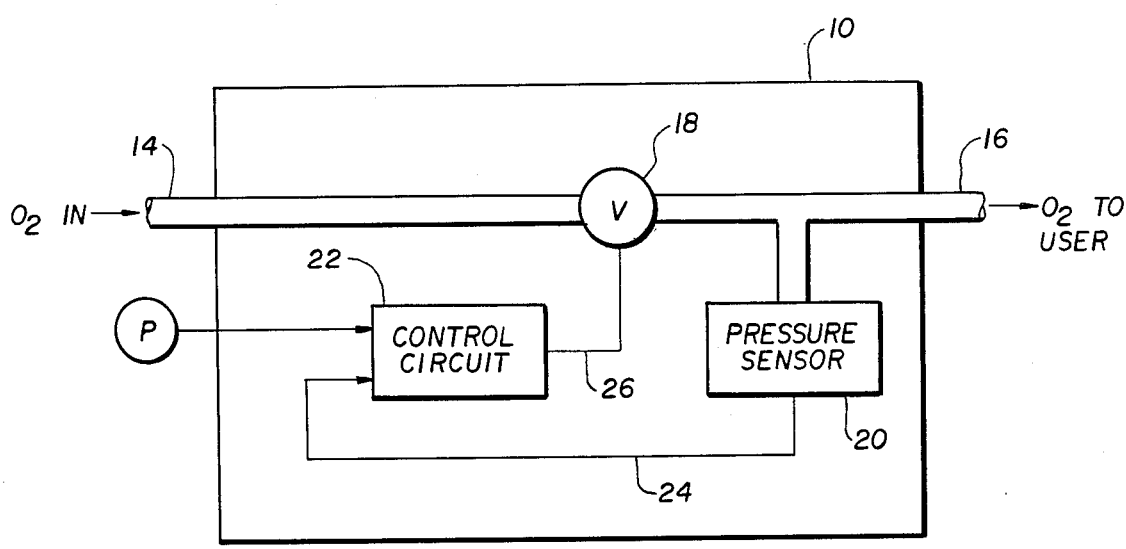
FIG. 2 is a simplified logic diagram of the invention flow controller.
Figure 3:
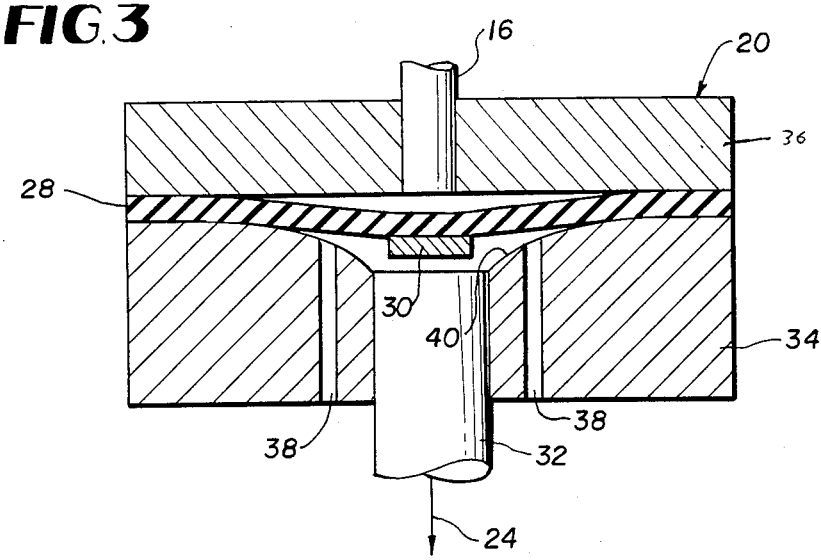
FIG. 3 is a partially schematic and partially vertical cross-sectional view through the invention pressure sensor.

Referring now to FIG. 2, the invention flow controller 10 comprises a solenoid valve 18 positioned between the intake line 14 and the delivery line 16. The on/off state of this valve 18 is controlled by a control circuit 22. Control circuit 22 is in turn controlled, at least in part, by an enabling signal from the invention pressure sensor 20. Pressure sensor 20 is shown in detail in FIG. 3, and control circuit 22 is shown in detail in FIG. 4. Power is delivered as indicated by the symbol "P" to the control circuit 22 in a conventional manner. A line 24 interconnects the pressure sensor 20 to the control circuit 22, and a line 26 connects the control circuit 22 to the solenoid valve 18 to control valve 18. As shown in FIGS. 2 and 3, oxygen delivery line 16 has a branch which exposes one side of the pressure sensor 20 to the delivery side pressure in the oxygen supply system of lines 14 and 16.

As to power requirements, since the successfully constructed embodiment of the invention depends upon digital logic, a regulated DC source is required. For stationary units having self-contained motor-compressor sets, AC power is conventionally used. Thus, if the invention flow controller will be physically integrated into the source 12, particularly where the source 12 is an oxygen concentrator, then it is an additional requirement, although a relatively simple one, to have a power supply integrated into the combination concentrator/flow controller, which will provide the necessary regulated DC power. In a machine that is portable, or in a machine that is normally stationary but portable in an emergency, suitable accommodations for supplying the necessary power can be easily made using battery type systems, as is well known to those skilled in these arts.

Referring now to FIG. 3, the sensor 20 is shown in some detail but still somewhat schematically. The sensor 20 includes a diaphragm formed of a suitable rubber or rubber-like material. The metal disk 30 is secured in a suitable fashion to one side of the diaphragm 28. A proximity switch 32, which is cooperative with the disk 30, is mounted in the lower body half 34 of the sensor 20. A complementary upper body half 36 is provided, and the delivery passageway 16 passes through this upper half 36 to expose the upper side of the diaphragm 28, the side thereof opposite the disk 30, to the pressure in the line 16. A pair of relief ports 38 are provided in the lower body half 34. The lower body half 34 is dished or beveled as indicated by the conical surface 40 which contains the openings of the relief ports, and which is also defined in part by the upper operative surface of the proximity switch 32.

Means, not shown, are provided to hold the body halves 34 and 36 in assembled together condition with the edges of the diaphragm 28 secured therebetween.

It should be noted that the diaphragm 28 is relatively loose in the sensor 20. That is, the diaphragm is mounted in the sensor in a slack, non-taut or relaxed manner. This is a significant aspect of the present invention, and achieves numerous advantages. The parts are adusted so that, as shown in FIG. 3, the disk 30 is shown in electrical proximity to the switch 32. Upon an inhalation breath from the user, which is indicated by double arrows in FIG. 1, this negative pressure will raise the diaphragm 28 in its loose unsecured center section together with the disk 30 upwardly. The parts are adjusted so that this motion will cause an electrical change of state in the switch 32 due to the metal disk 30 going out of proximity with respect to the switch 32. The looseness of the diaphragm permits very slight pressures to cause this motion of the diaphragm and the disk. The size and weight of the disk 30 are made to be the minimum possible, with respect to the necessary operating parameters of the proximity switch 32, to further assist in this advantageous manner of operation. Other means in the control circuit 22, shown in FIG. 4 described below, ensure that the loose diaphragm will not cause any undesirable operating characteristics. The dished surface 40 prevents any sharp edges or the like from adversely affecting the loose diaphragm 28. In fact, experiments have shown that the arrangement shown in FIG. 3 can operate with an acceptably long useful life at operating pressures in the line 14 of as high as 50 PSI. The relief ports 38, which are exposed to atmosphere, permit equalization of pressure on the diaphragm when negative pressure or positive pressure impinges on the upper side of the diaphragm.

Experiments have shown that the loose diaphragm of FIG. 3 is not as susceptible to vibration caused by the oxygen flows in the line 16 as are prior art devices which include a taut, stretched or otherwise tightly held diaphragm 28. These prior art devices have been found to vibrate vigorously in response to surges of oxygen within the line 16, these vibrations being highly undesirable and difficult to accommodate in the remainder of the apparatus. Elimination of this vibration by the loose diaphragm 28 is an important advantage of the invention.

Looking at this another way, the loose diaphragm ensures that the motion of the disk 30 away from the switch 32 is caused only by an inhalation of the patient, and not by any other cause, and it is that response which is necessary for proper operation of the invention flow controller overall The loose diaphragm produces another important advantage. By physically positioning the proximity switch appropriately, and due to the cooperation thereof with the loose diaphragm 28, the sensor 20 can be made to produce a signal on the line 24 directed to the control circuitry 22 either at the beginning of inhalation as described above, or at the end of an exhalation breath. This versatility of arrangement of the parts and the circuitry is deemed to be an important advantage of the invention which could come into play in other environments.

In experimental work done in developing the present invention, it has been found that, all other things being equal except for the presence of the dished surface 40, the sensor 20 would operate satisfactorily only up to pressures of approximately 8 PSI. With this surface 40, pressures on the order of 50 PSI can be successfully accommodated.

The minimization of the size and weight of the disk 30 is important since the entire diaphragm, at least the loose moving part of it, together with the disk 30, must be accelerated solely in response to the negative pressure caused by an inhalation breath of the patient. Since the patients are often very sick persons, these pressures can be very weak, and thus the need for the sensitivity of the invention. In addition, the sensitivity of the invention is so much improved over the prior art that it has been found to work satisfactorily with a patient using only a cannula as opposed to a mask. As stated above, the invention can be used with a mask as well, but it is an important improvement of the invention that it can work with a cannula.

The invention is to be contrasted with prior art arrangements wherein the negative pressure impinges on the diaphragm on the same side thereof as the switch. That is, the negative pressure pulls the diaphragm into proximity with the switch. In the present invention, the negative pressure pulls the diaphragm out of proximity to the switch. This is important for several reasons including the flutter or vibration effect discussed above.

In summary, the invention produces an interaction of the small weight and mass of the disk 30 together with the relatively large surface area of the diaphragm exposed to the negative pressure from the line 16. This, together with other features of the invention, produces a highly sensitive pressure sensor adaptable for successful use in the invention's environment, even with a patient cannula.

Figure 4:
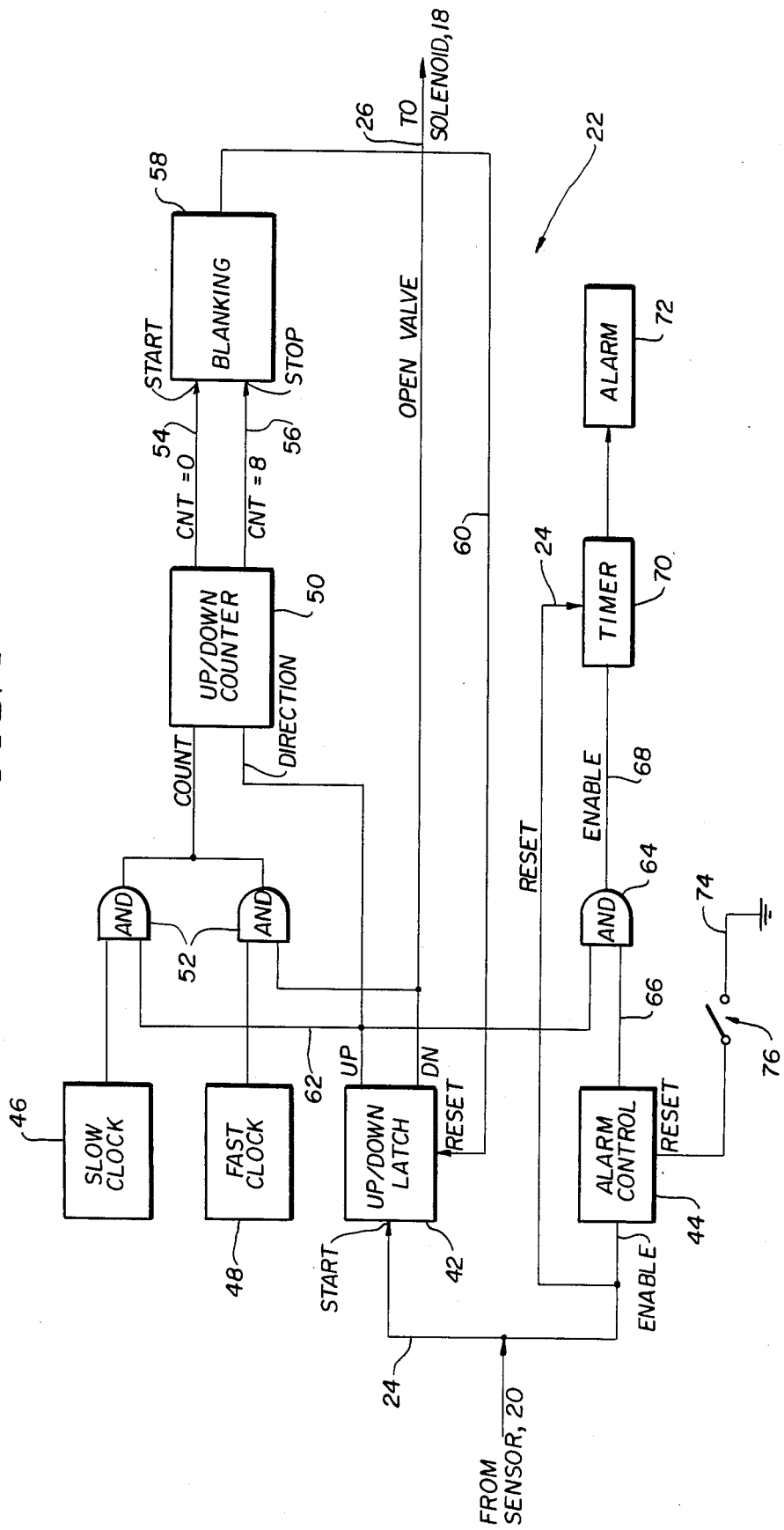
FIG. 4 is an electrical schematic drawing of the invention control circuitry.

Referring now to FIG. 4, there is shown a schematic diagram of the control circuit 22. Overall, signals on line 24 from the pressure sensor 20 pass through the circuitry 22, and exit on the line 26 to control the on/off state of the valve 18. In addition, alarm means are also actuated by the signals on the line 24.

Turning now in more detail to FIG. 4, the signals on the line 24 first enter, simultaneously via branches thereof, an up/down latch 42 and an alarm control 44. The alarm branch of the circuitry will be described below.

The control part of the circuitry is based on a pair of "clocks" 46 and 48, each of which is adjustable. Because, as described above, normal breathing has a ratio of duration times of approximately 2:1 of exhalation to inhalation, the slow clock 46 is made to operate at a rate or frequency which is half that of the fast clock 48. Both clocks 46 and 48 are adjustable, and thus it is a relatively simple matter to achieve some ratio other than 2:1 if that should be desired because of the needs of a particular patient or of a different environment. The pulses from one or the other of the clocks 46 and 48 are directed to an up/down counter 50 via a steering circuit made up of the latch 42 and a pair of "AND" gates 52. A pair of lines 54 and 56 deliver predetermined pulses to a blanking circuit 58, and the output of the blanking circuit 58 is directed by a line 60 to the "RESET" terminal of latch 42. The line 26 extends from the latch 42 to the solenoid valve 18. The manner of operation of this control circuitry will appear below.

Another multi-branching line 62 extends from the latch 42 to one of the AND gates 52, to the direction-controlling terminal of the counter 50, and to another AND gate 64 in the alarm branch of the control circuitry 22.

A line 66 from the timer 44 provides a second input to AND gate 64. An output line 68 enables a timer 70 which in turn controls an alarm 72. Another branch of line 24 also delivers the signal from sensor 20 to timer 70. A line 74 which goes to ground contains a manual switch 76 which connects to the RESET terminal of the timer 44. The alarm 72 can be an audible alarm, a visible alarm, or both, as is conventional in these arts.

One problem to which this alarm portion of the circuitry of FIG. 4 is directed is to detect an apnea or "sudden death" occurrence. However, an alarm will be triggered at any time that one inspiration pulse does not follow another by the time set on the timer 70, and thus it is not truly accurate to call this portion of the FIG. 4 circuitry an apnea alarm. It will alarm if an apnea episode occurs, but an alarm does not necessarily mean that an apnea episode has occurred. As another example, the alarm will sound if the nasal cannula should accidentally fall from the user's nose or accidentally become disconnected from the machine, and that certainly is not an apnea emergency.

Thus, in summary, just as the present invention can be thought of, inaccurately, as a demand valve when in fact it is a flow controller, the alarm portion could, incorrectly, be thought of as an apnea alarm, when, more accurately, it is really a flow control monitor alarm.

OPERATION

The manner of operation of the invention will now be described together with a description of FIGS. 5 and 6.

Figure 5:
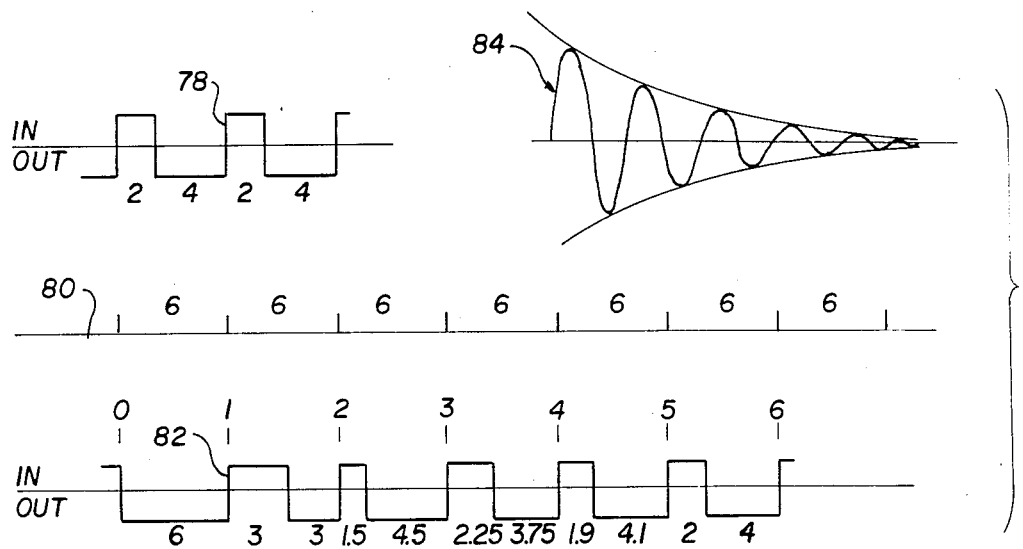
FIG. 5 shows a family of curves which illustrate the "homing" feature of the invention.

Referring now to FIGS. 4 and 5, the manner in which the control circuitry 22 of FIG. 4 causes the frequency and durations of the periods of supplying oxygen and not supplying oxygen to match the breathing cycle of the user is illustrated.

For the sake of this example, the line 80 on FIG. 5 indicates that the patient is taking an inspiration once every six seconds. Other patients might breathe faster or slower, and the rate may change with time and the activity of the patient. Further, the patient may experience aberrations or temporary changes in his breathing pattern. As will appear from the description below, the control circuitry of FIG. 4 will accommodate all of these occurrences and will maintain a 2:1 ratio of the duration times of exhalation time to inhalation time. The curve 78 shows, for this six-second cycle, the ideal situation of two seconds' inhalation (IN) and four seconds' exhalation (OUT). This 2:1 ratio has been found to be substantially accurate for most people. It can be changed, since both clocks 46 and 48 are adjustable. Further, if the patient had, for example, a nine-second cycle, the inhalation time would be three seconds and the exhalation time six seconds.

The curve 82 shows how the circuitry of FIG. 4 accommodates the worst possible case, that is, the situation where, upon start-up, the patient was taking an inhalation breath, and the machine happened to start up at an exhalation point. Changes of state, that is the latch 42 changing state, occur only upon sensing an inhalation. Thus, in this harsh condition, in the first cycle, the patient would be provided no oxygen for the entire six seconds. This is not life-endangering in any way, since the patient in most cases is using a cannula and can breathe through his mouth. Even where he is using a mask, the mask will have accommodation to permit the patient to breathe normal air. During exhalations, the steering circuit made up of the latch 42a, the AND gates 52 Control Counter 50 by providing a signal on its branch of the line 62 causing it to count up. The steering circuit (parts 42 and 52) direct the pulses from the slow clock 46 (which can be thought of as the exhalation clock), and a certain count will be generated. At the end of the exhalation according to the circuitry, which corresponds to the end of the first cycle marked "1" on curve 82, an inhalation will occur. This pulse will be delivered on line 24 to the latch 42, and the steering circuit will direct pulses from the fast or inhalation clock 48 to the counter. Simultaneously, the counter 50 will count down. Since the ratio of the frequencies of the two clocks 46 and 48 is 2:1, the clock will count down to zero in exactly half of whatever time was required for the slow clock 46 to generate that same count. Further, the act of changing state of the latch 42 from providing a pulse on the branching line 62 to providing a pulse on the branching line 26 sends an output signal to the solenoid valve to open and cause oxygen to be supplied to the patient for the period of time determined by the time the fast clock 48 is running and until it counts down the count on the counter 50. When the countdown is finished, a signal is put out through the lines 54 or 56 through the blanking circuit 58 (the operation of which is described below) and feeds back through the line 60 to the latch 42 to reset it. This again causes the steering circuit 42–52 to change state, and removes the signal on the line 26, thus stopping the flow of oxygen to the user.

Thus it can be seen that the period of providing oxygen will always be equal to half of the period next preceding when oxygen was not supplied.

The curve 82 of FIG. 5 should now be clear. The first exhalation period, the harsh and worst possible case, provided six seconds of exhalation. Thus the next inhalation period will be three seconds long and the next exhalation period will be the remainder of the six-second cycle, that is, the time to the next inhalation breath or three seconds. The third cycle will then have an inhalation period of 1.5 seconds, leaving an exhalation period of 4.5 seconds. And so on through the various periods, it being clear that the time of inhalation and exhalation rapidly approaches the ideal of 2:1. The curve 84 on FIG. 5 shows this occurrence in another manner. The effect is virtually identical to a damped sinusoidal curve, and it rapidly "homes".

As to the rapidity of the "homing", experiments performed during the development of the invention have shown that the circuitry will always correct itself within five cycles. In the example given, this is an insignificant period of time; namely, five cycles times six seconds per cycle, or thirty seconds total, until the patient's breathing is matched by the invention device. Even accommodating other types of irregularities in breathing, slower periods of time, and the like, this experimentation has shown that the invention will, without fail, match any breathing pattern in less than one minute.

A certain characteristic of the human body aids the invention in meeting the patient's needs quickly. For complex medical reasons not germane to this disclosure, the human body gets more benefit from the early part of an inhalation breath than it does from the later part. Thus, if any oxygen at all is supplied, even substantially less than two seconds' worth as set forth in the example, still the patient's need will be well served since his body gets the most benefit from the early part of each breath.

If a patient should have an unusual breathing pattern, such as, for example, half the time inhalation and half the time exhalation, then the rates of the two clocks 46 and 48 would be made equal, and that would be automatically accomodated. In a similar manner, any other ratio of inhalation to exhalation during a breathing cycle would be accommodated in the same way.

For safety purposes, the solenoid valve 18 is preferably arranged to be normally open. That is, when power is applied via line 26, the valve will close for the exhalation cycle. However, in the event of a power failure or any other failure, the valve 18 will ultimately come to its open condition, thus not depriving the user of oxygen from the regulated source 12.

As is clear, the invention has been arranged as to electrical "polarity" in a certain manner, as this has been found to be advantageous in this particular environment. The actions in response to the change of state of the latch 42, the manner in which the disk 30 operates the switch 32, the normally "on" or normally "off" state of the switch 32, and other such polarity-type considerations as to the circuitry are easily adjusted by those skilled in the art to accommodate any particular need or other environment.

The lower half of the circuit of FIG. 4 illustrates the manner of operation of the invention alarm. It is anticipated that an alarm would not be needed in portable equipment, since in that situation the patient is awake, unlikely to fall asleep, and the alarm adds weight to the apparatus as well as power consumption. There is conceptually, however, no reason why an alarm such as is shown in FIG. 4 could not also be used in portable equipment or in equipment designed for both portable and stationary use, if it should be desired.

Overall, the alarm circuitry will activate the alarm 72 if it does not receive an inhalation signal on a regular basis; 30 seconds has been selected more or less arbitrarily.

The inhalation pulses on the line 24 are used to RESET the timer 70. Failure to receive such a pulse within the countdown time (30 seconds) of the timer 70 will cause the timer 70 to activate the alarm 72.

Means are also provided to permit the user to temporarily stop using the invention device and to prevent the alarm from sounding during such period. In addition, these same means will permit, upon the user's resuming use of the invention device, or upon the user's first use after a long period of no use (i.e., start-up), his next inhalation to automatically activate the alarm again.

More specifically, when the user temporarily (or otherwise) discontinues use, he will remove his cannula and activate the manual reset button 76. This will reset the alarm control 44 and leave it inactive until it is again enabled. This removes the signal on the line 66 to the AND gate 64. When the user resumes use, the next inhalation breath on line 24 will again enable the alarm control device 44, providing a signal on line 66. Thereafter, the normal cycle will be resumed, and each signal on the line 62 corresponding to an exhalation will provide an enabling signal 68 to the timer 70, and each inhalation breath will reset the timer 70 via its branch of line 24.

If the user should suffer some medical emergency, the failure of an inhalation breath after the period of time of the counter 70 will activate the alarm 72.

In a similar manner, if the machine is first turned on but the user does not commence use, the alarm 72 will not be activated, since an inhalation breath is required to enable control 44 which in turn enables timer 70 on line 68.

Figure 6:
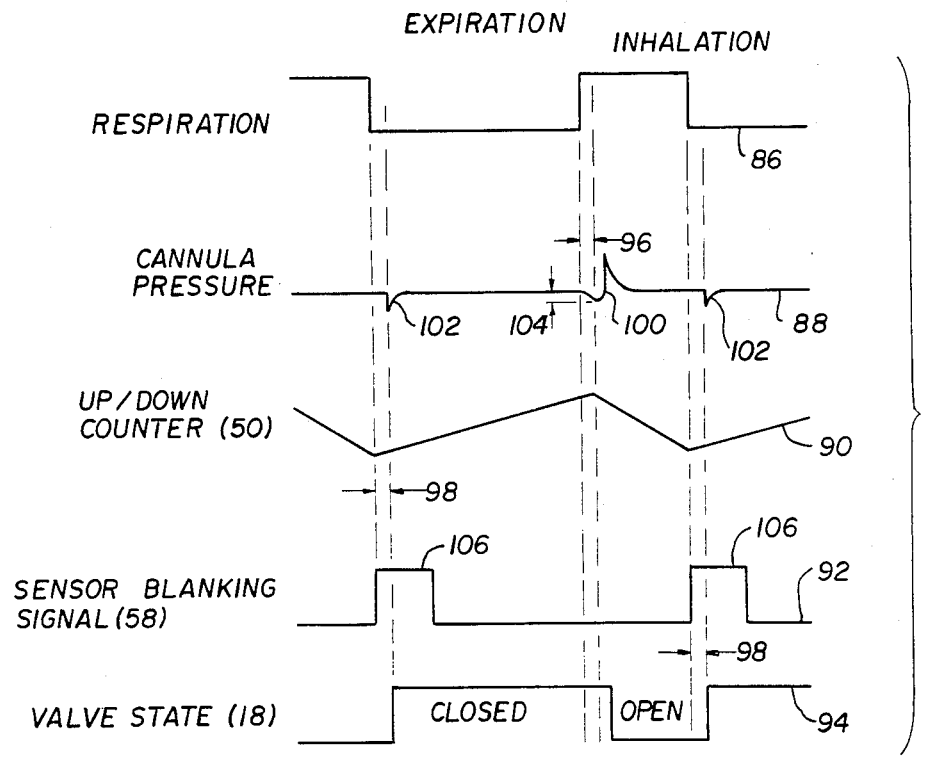
FIG. 6 is a family of curves which illustrate the timing relationships of the various parts of the invention device.

Referring now to FIG. 6, there is shown a family of curves 86, 88, 90, 92, and 94 which illustrate the manner of operation of the invention and will be useful in understanding the purpose and function of the blanking circuit 58 in FIG. 4. The five curves are arranged in proper relationship to each other on a time axis which extends horizontally. The vertical dotted lines interconnecting the curves will aid in understanding.

The curve 86 shows the patient's breathing, and corresponds conceptually to the curve 78 of the FIG. 5.

The curve 88 is the actual pressure in the cannula caused by the patient's breathing. The segment of the curve 100 is the actual inspiration breath. The time indicated at 96 corresponds to the response time of the sensor 20; that is, the time between the actual inhalation indicated by the rising segment of the curve 86 and the sensing thereof in the cannula as indicated by the curve segment 100. Curve segment 100 represents the pressure in the cannula during an actual inspiration breath.

The curve 90 is a schematic representation of the accumulation of pulses, the actual representation would, of course, be stepped, due to the use of digital pulses in the counters.

The two curve segments 102 are false negative pressure pulses which can adversely affect the operation of the invention. These false pulses are created by the back pressure which is created by the closing of the valve, indicated by the rising segment of the curve 84. More specifically, this false pressure pulse 102 is created when the valve 18 closes because the oxygen suddenly flowing out of the cannula suddenly is not replenished by any inlet flow. This results in the slight temporary negative pressure until the system stabilizes. It is that false negative pressure pulse 102 which is accommodated by the blanking circuit 58 as indicated by the curve 92 as described below. The distance 98 is the response time between the appropriate segments of the curves 86 and 94, as shown. It should be noted that the height 104 of the true curve segment 100 is approximately equal to the height of the false pulse 102. Thus, the false pulse 102 would be sufficient to activate the latch 42 (FIG. 4) to thus cause improper operation of the invention. The blanking circuit 58 produces the segments 106 of the curve 92 which overlay in time the occurrence of the false pulses 102. These segments 106 lock out or block the resetting of the latch during this period so that the false pulse 102 cannot operate the latch 42.

The way this is done is indicated by the lines 54 and 56. Eight counts have been arbitrarily selected during which time the blanking circuit is activated to perform the function indicated by the curved segments 106 in FIG. 6. Depending upon the particular frequencies of the two clocks 46 and 48, this arbitrary number of eight counts would be adjusted accordingly. More specifically, the first pulse on the line 54 enables the blanking circuit 58, but it is only the pulse produced by the eighth count on the line 56 which actually produces the reset signal on the line 60. In this manner, the latch 42 is disenabled during the time the false pulses 102 occur.

While the invention has been described in some detail above, it is to be understood that this detailed description is by way of example only, and the protection granted is to be limited only within the spirit of the invention and the scope of the following claims.

We claim:

1. A flow controller for use in supplying gas from a source to a user, said flow controller comprising means to supply said gas to said user during periods of the user's breathing inhalations and to not supply said gas to said user during periods of the user's breathing exhalations, said supply means comprising means to match the durations of said inhalation and exhalation periods to the user's actual breathing pattern based on a predetermined ratio of inhalation and exhalation duration times; said supply means comprising valve means, control means for said valve means and sensor means for sensing each inhalation breath of the user; said control means comprising circuit means comprising up/down counter means, first and second clock means, and steering circuit means for directing the pulses from one or the other of said first and second clock means to said up/down counter means; means to direct control signals from said control means to said valve means, means to direct pulses from one of said first and second clock means via said steering circuit means to said counter means to cause said counter means to count up from starting counting point, and means to direct pulses from the other of said first and second clock means via said steering circuit means to said counter means to cause said counter means to count down from the count generated by said pulses from said first-mentioned one of said clock means back towards said starting counting point, means to cause said control means to generate said control signal for said valve means when the count of said counter means comes to said starting counting point, and means to cause the ratio of the frequencies of pulse production from said first and second clock means to equal said predetermined ratio of the inhalation and exhalation duration times of the user's breathing pattern.

2. The flow controller of claim 1, wherein said equal ratio is 2:1 exhalation to inhalation, and wherein said steering circuit and said first and second clock means cause the duration of each period when said valve means supply gas from said source to said user to equal half of the duration of the immediately preceding period when no gas was supplied to said user, and said control means comprising means to cause the total duration time of each pair of a gas supply period and a no gas supply period, one following the other, to equal the time between two succeeding inhalation breaths of said user.

3. The flow controller of claim 1, wherein said gas is oxygen, said source is an oxygen concentrator, and said user is a respiratory patient.

4. The flow controller of claim 1, said supply means comprising a nasal cannula.

5. In combination, a sensor for use in a flow controller to supply gas from a source to a user, said sensor comprising means for sensing each inhalation breath of the user, said sensor means comprising a diaphragm and sensor body means, means to mount said diaphragm in said body means so that the operative portion of said diaphragm is loosely mounted in said body means, proximity switch means, means to mount said proximity switch means in said body means in predetermined closely spaced relation to said diaphragm, disc means, means to mount said disc means on said diaphragm on the side of said diaphragm facing said proximity switch means, means to direct negative pressure produced by each inhalation breath of the user into said body means, means to expose the side of said diaphragm opposite the side thereof which carries said disc and which is exposed to said proximity switch means to said negative pressure, control means to produce a control signal in response to the sensing of said negative pressure by said sensor means, and means responsive to said control signals to prevent the supplying of said gas from said source to said user at predetermined times in said user's breathing pattern when spurious motions of said loose diaphragm would cause said control means to produce corresponding spurious signals.

6. A method for supplying gas from a source to a user during periods of the user's breathing inhalations and for not supplying said gas from said source to said user during periods of the user's breathing exhalations, comprising the steps of using valve means to control the supply of gas from said source to said user, using control circuit means to operate said valve means, determining a ratio of the durations of said inhalation and exhalation periods, generating an inhalation signal corresponding to each inhalation breath of the user, feeding said inhalation signals to said control circuit means, causing counter means in said control circuit means to count in one direction during each exhalation breath of the user and stopping said counter means counting in said one direction upon receipt of each said inhalation signal, thereafter causing said counter means to count in a direction opposite said one direction, causing the duration time of said counting in said opposite direction to be related to the duration time of the counting in said one direction and to said ratio, matching the durations of said inhalation and exhalation periods to the user's actual breathing pattern based on said ratio, and supplying said gas during said inhalation periods and not supplying said gas during said exhalation periods.

7. The method of claim 6 wherein said ration is 2:1, exhalation to inhalation.

8. The method of claim 6, and the step of disabling the feeding of said inhalation signals to said control circuit means at a selected time in the user's breathing cycle at means spurious signals which would otherwise create false control signals are likely to be fed to said control circuit means.

9. The method of claim 6, wherein said gas is oxygen, and the step of supplying the oxygen from the source to the user via a nasal cannula.

* * * * *